United States Patent
Caspers

(10) Patent No.: US 10,850,028 B2
(45) Date of Patent: Dec. 1, 2020

(54) TRIGGERING INJECTION STATUS INFORMATION DISPLAY ON A MOBILE DEVICE VIA TAPPING THE HOUSING OF A SKIN-ATTACHABLE DRUG INJECTION DEVICE

(71) Applicant: Sanofi, Paris (FR)

(72) Inventor: Michael Caspers, Frankfurt am Main (DE)

(73) Assignee: Sanofi, Paris (FR)

( * ) Notice: Subject to any disclaimer, the term of this patent is extended or adjusted under 35 U.S.C. 154(b) by 291 days.

(21) Appl. No.: 15/510,288

(22) PCT Filed: Sep. 11, 2015

(86) PCT No.: PCT/EP2015/070874
§ 371 (c)(1),
(2) Date: Mar. 10, 2017

(87) PCT Pub. No.: WO2016/041875
PCT Pub. Date: Mar. 24, 2016

(65) Prior Publication Data
US 2017/0258987 A1     Sep. 14, 2017

(30) Foreign Application Priority Data

Sep. 15, 2014   (EP) ..................... 14306423

(51) Int. Cl.
*A61M 5/142*   (2006.01)
*A61M 5/145*   (2006.01)
*A61M 5/20*    (2006.01)
*G06F 1/16*    (2006.01)
*A61M 5/31*    (2006.01)

(52) U.S. Cl.
CPC ...... *A61M 5/14248* (2013.01); *A61M 5/1452* (2013.01); *A61M 5/20* (2013.01);
(Continued)

(58) Field of Classification Search
CPC .. A61M 5/14248; A61M 5/20; A61M 5/1452; A61M 2205/8206;
(Continued)

(56) References Cited

U.S. PATENT DOCUMENTS 5,782,805 A * 7/1998 Meinzer .............. A61M 5/172
                                              604/131
6,589,229 B1   7/2003 Connelly et al.
(Continued)

FOREIGN PATENT DOCUMENTS

CN   101185079   5/2008
EP   2131263    12/2009
(Continued)

OTHER PUBLICATIONS

Diabetes Education Online, "What is an Infusion Set?", (Jul. 27, 2013), <URL https://dtc.ucsf.edu/types-of-diabetes/type2/treatment-of-type-2-diabetes/rnedications-and-therapies/type-2-pump-rx/how-to-use-your-pump/what-is-an-infusion-set/>, pp. 1-2 (Year: 2013).*
(Continued)

*Primary Examiner* — Ajay M Bhatia
*Assistant Examiner* — Mong-Shune Chung
(74) *Attorney, Agent, or Firm* — Fish & Richardson P.C.

(57) ABSTRACT

A skin attachable drug injection device (1), comprising an accelerometer (26) able to detect the user tapping against the housing (2) of the device and to generate an electrical signal to the device controller (16), which recognizes the signal as a user request for information regarding the ongoing delivery of the medicament, and a transmitter (30) which in response wirelessly transmits said information (e.g. the expected remaining during of the injection) to a separate portable user device having a display (e.g. mobile phone). A
(Continued)

user carrying the injection device under clothing can thus receive feedback about the status of the injection in a discreet way.

25 Claims, 5 Drawing Sheets

(52) U.S. Cl.
CPC . *G06F 1/1613* (2013.01); *A61M 2005/14252* (2013.01); *A61M 2005/14268* (2013.01); *A61M 2005/3126* (2013.01); *A61M 2205/18* (2013.01); *A61M 2205/332* (2013.01); *A61M 2205/3561* (2013.01); *A61M 2205/3584* (2013.01); *A61M 2205/3592* (2013.01); *A61M 2205/502* (2013.01); *A61M 2205/581* (2013.01); *A61M 2205/582* (2013.01); *A61M 2205/583* (2013.01); *A61M 2205/8206* (2013.01); *G06F 2200/1636* (2013.01)

(58) Field of Classification Search
CPC .... A61M 2205/3584; A61M 2205/582; A61M 2205/581; A61M 2205/3592; A61M 2205/583; A61M 2205/3561; A61M 2205/332; A61M 2205/18; A61M 2205/502; A61M 2005/14252; A61M 2005/3126; A61M 2005/14268; G06F 1/1613; G06F 2200/1636
See application file for complete search history.

(56) References Cited

U.S. PATENT DOCUMENTS

| | | | |
|---|---|---|---|
| 2006/0229557 A1* | 10/2006 | Fathallah | G06F 19/00 604/131 |
| 2006/0264835 A1* | 11/2006 | Nielsen | A61M 5/14248 604/174 |
| 2008/0091175 A1* | 4/2008 | Frikart | H04L 63/061 604/891.1 |
| 2011/0105955 A1* | 5/2011 | Yudovsky | G01P 15/0802 600/595 |
| 2012/0068850 A1 | 3/2012 | Ito | |
| 2012/0154292 A1 | 6/2012 | Zhao et al. | |
| 2013/0133427 A1 | 5/2013 | Yudovsky et al. | |
| 2013/0141329 A1 | 6/2013 | Halbert et al. | |

FOREIGN PATENT DOCUMENTS

| | | |
|---|---|---|
| JP | 2002-126092 | 5/2002 |
| WO | WO 2006/108304 | 10/2006 |
| WO | WO 2012/090296 | 7/2012 |
| WO | WO 2014/037331 | 3/2014 |
| WO | WO 2015/038588 | 3/2015 |

OTHER PUBLICATIONS

Neithercott, "Sticking Tips for Infusion Sets", (Jan. 2013), <URL http://www.diabetesforecast.org/2013/jan/infusion-sets-2013.html/>, pp. 1-4 (Year: 2013).*
Boland et al., "Finding my beat: Personalized Rhythmic Filtering for mobile Music Interaction," Mobile HCI Aug. 28, 2013, pp. 21-30.
Extended European Search Report in European Application No. 14306423.6, dated Jun. 8, 2015, 16 pages.
International Preliminary Report on Patentability in International Application No. PCT/EP2015/070874, dated Mar. 21, 2017, 12 pages.
International Search Report and Written Opinion in International Application No. PCT/EP2015/070874, dated Dec. 1, 2015, 19 pages.

* cited by examiner

TRIGGERING INJECTION STATUS INFORMATION DISPLAY ON A MOBILE DEVICE VIA TAPPING THE HOUSING OF A SKIN-ATTACHABLE DRUG INJECTION DEVICE

CROSS-REFERENCE TO RELATED APPLICATIONS

This application is a U.S. national stage application under 35 USC § 371 of International Application No. PCT/EP2015/070874, filed on Sep. 11, 2015, which claims priority to European Patent Application No. 14306423.6 filed on Sep. 15, 2014, the entire contents of which are incorporated herein by reference.

FIELD

This specification relates to providing feedback to a user regarding delivery of a medicament. Particularly, but not exclusively, the specification relates to an injection device which responds to a physically input request at the device by providing feedback to a separate user device.

BACKGROUND

Wearable devices for delivering medicament to a patient are sometimes worn by the patient for a significant length of time in order to allow the medicament to be delivered at a desired rate or over a desired time period. An example of this type of wearable device is a bolus injector, which is typically worn like a patch against the skin. A bolus injector generally carries out automated subcutaneous delivery of relatively large volumes of liquid medicament to the patient, such as at least 1 ml. Such bolus injector devices can be called large volume devices (LVDs). The delivery of the medicament can last for several minutes or hours and so the patient may wear the device under his or her clothing during the course of the day. The patient generally does not know the status of the device and does not know how the delivery of medicament is progressing.

SUMMARY

The invention solves problems with previous devices by providing feedback to the user in a discreet manner. This gives privacy to the user and prevents other persons, for example, in the vicinity of the user, being made aware of the feedback. Feedback given by other techniques, such as sounds or vibrations, would suffer from being non-discreet and would therefore not maintain privacy for the user of the device.

According aspects of the invention, there is provided a device configured to deliver a medicament to a user by injection, comprising a transducer configured to detect a physical input to the device during an injection and to generate a signal which is indicative of the detected physical input; a feedback apparatus configured to respond to the signal by recognizing the physical input as being a user request for information regarding delivery of the medicament; and a transmitter configured to respond to the request by outputting information regarding the delivery of the medicament to a separate user device via a wireless communication link.

These features of the device may allow a user of the device to request feedback about an injection in a discreet manner. The features may also allow the device to provide the feedback in a discreet manner to a user device, such as a smart phone.

The device may further comprise a housing with a contact region arranged to be worn against the skin of the user, wherein the transducer is configured to detect a physical input to the housing during an injection and to generate said signal which is indicative of the detected physical input.

In one embodiment, the device further comprises an injection element that protrudes out of the contact region of the housing. The injection element may be extendable and/or retractable from the housing.

The device may further comprise a fastener that is configured to hold the contact region against the skin of the user. The fastener may comprise an adhesive layer.

The device may further comprise a reservoir for medicament that is disposed in the housing.

The transducer may comprise a motion sensor configured to detect motion of the device caused by the physical input and to generate the signal as being indicative of the detected motion of the device.

The signal indicative of motion of the device may allow the device to differentiate between different types of motion and thus different types of input.

The motion sensor may comprise an accelerometer.

Accelerations of the device may be detectable by the accelerometer and may be an effective way to differentiate between different physical inputs on the housing of the device.

The transducer may comprise an actuatable switch on a housing of the device.

The actuatable switch may provide a way in which the user can give physical inputs to the device. The switch may provide an effective implementation of the motion sensor.

The feedback apparatus may comprise a memory in which is stored data linking at least one stored physical input with at least one stored user request.

These memory links may allow the device to recognize a physical input as a request for feedback.

The feedback apparatus may be configured to recognize the physical input as being the user request by accessing the memory to identify a link between the detected physical input and a stored user request.

This may allow the device to recognize different user requests and differentiate between them.

The physical input may comprise at least one tap on a housing of the device.

This is an example of way in which the user may provide an input in a discreet manner. It may also provide ease of operation for the user.

The feedback apparatus may be configured to recognize the user input as being a request for an indication of the remaining duration of the injection.

This may improve the usability of the device by allowing the user to request the time remaining before completion of the injection. This may reduce mental stress on user.

The transmitter may be configured to output the information by searching for nearby user devices and transmitting the information to the closest user device identified in the search.

This may provide a secure way in which feedback can be transmitted to the user's user device without being received by other devices.

The transmitter may be configured to precede outputting the information by initiating a wireless pairing process with the user device.

This may improve security by transmitting the feedback only to the paired user device.

The transmitter may be configured to transmit the information regarding the delivery of the medicament together with a unique identifier of the device.

This may allow secure communication with a user device, for example via a web server.

The transmitter may be configured to output the information in an encrypted form.

This may improve the security of the transmission of feedback.

According to aspects of the invention, there is provided the device and an application program for the user device which, when executed by a processor in the user device, causes the information output by the transmitter to be displayed.

According to aspects of the invention, there is provided a system comprising the device and a reservoir of medicament to be delivered into the user by injection.

According to aspects of the invention, there is provided a method of outputting information regarding the delivery of a medicament from a device configured to deliver the medicament to a user by injection, comprising: detecting a physical input to the device during an injection; generating a signal which is indicative of the detected physical input; responding to the signal by recognizing the physical input as being a user request for information regarding delivery of the medicament; and responding to the request by outputting information regarding the delivery of the medicament to a separate user device via a wireless communication link.

In one embodiment, the device comprises a housing with a contact region arranged to be worn against the skin of the user, wherein the method comprises positioning the housing such that the contact region is located against the skin of the user, and wherein the step of detecting a physical input to the device during an injection comprises detecting a physical input to the housing during an injection The device may be wearable. This may allow the device to be fastened to the patient during an injection.

The device may be configured to transmit the feedback over the Internet.

The application program may contain an encryption key for decrypting the information outputted by the transmitter for display.

This may improve the security of the transmission of feedback between the device and the user device.

The device may be a bolus injector.

BRIEF DESCRIPTION OF THE FIGURES

For the purpose of example only, embodiments are described below with reference to the accompanying figures in which.

DETAILED DESCRIPTION

A fluid delivery device for delivering fluid medicament to a patient is described below. The device comprises a reservoir for storing a quantity of medicament and a dispensing interface for delivering the medicament to the patient. The device is configured to deliver the medicament from the dispensing interface by injection and to respond to physical inputs at the device by transmitting information regarding the injection to a separate user device. The injection and the transmission of the information can take place whilst the device is being worn against the patient's skin. In other embodiments, the delivery device can include an autoinjector or a pen injector.

Figure 1:
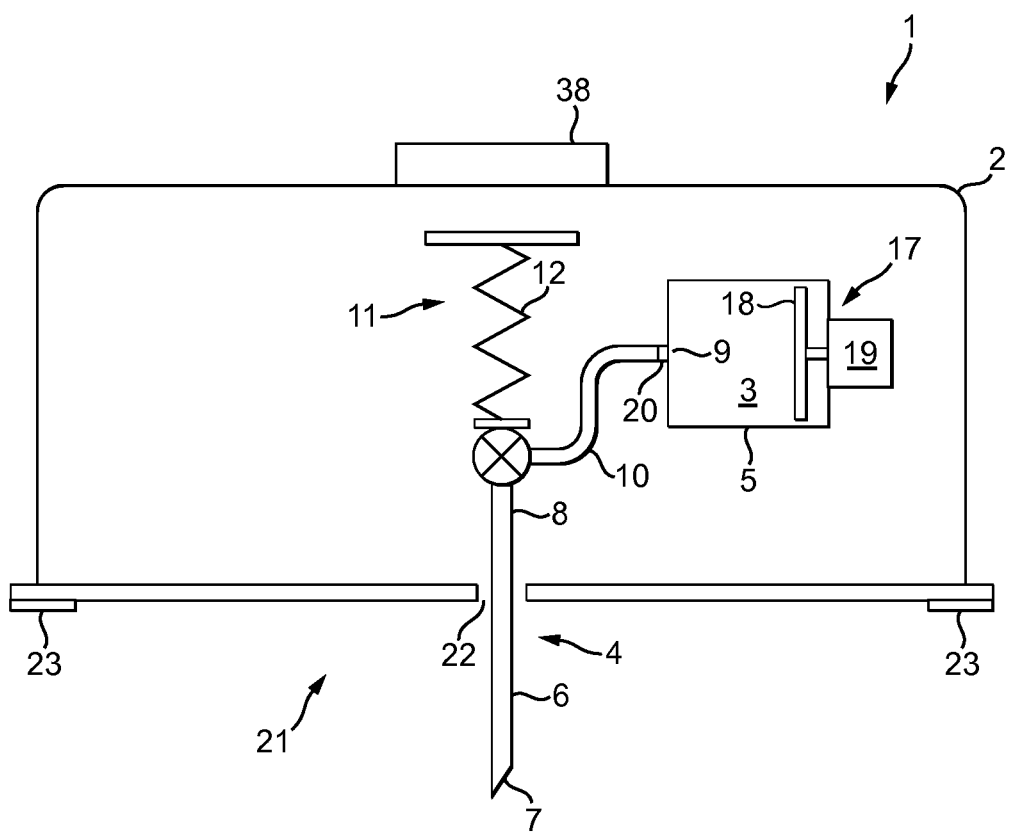
FIG. 1 is a schematic illustration of a wearable device for delivering medicament to a user by injection and providing discreet feedback to the user regarding the injection.

The device is described below in the context of a bolus injector, but it will be appreciated that it could alternatively be another type of Large Volume Device (LVD). Referring to FIG. 1, the device 1 comprises a protective housing 2 in which the reservoir of medicament 3 and the dispensing interface 4 are located together with other components of the device 1. The housing 2 is formed from moulded plastics or another suitable material. The reservoir of medicament 3 is provided in a capsule 5, which may contain a single dose of the medicament. The capsule 5 is formed of inert material such as glass and is secured inside an internal cavity of the housing 2. The capsule 5 may be replaceable to allow re-use of the device 1. Alternatively, the capsule 5 may be non-replaceable in the device 1 so that, once the contents of the capsule 5 has been exhausted, the device 1 can no longer be used to deliver medicament and must be disposed of.

This single-use nature of the device 1 facilitates ease of operation and improves safety by ensuring that a patient cannot mistakenly install an incorrect replacement capsule.

The dispensing interface 4 comprises an injection element for injection of the medicament from the device 1 into the patient. The injection element is explained below in the context of a cannula 6, as illustrated in FIG. 1, although it will be appreciated that other types of injection element could alternatively be used. Examples of alternative injection elements are discussed further below.

The cannula 6 comprises a distal end 7, which during use protrudes through the housing 2 of the device 1 into the body tissue of the patient. The cannula 6 also comprises a proximal end 8, which is arranged to receive medicament from the reservoir 3 referred to above. For example, an opening 9 in the form of an exit port in the capsule 5 may allow medicament to flow out of the capsule 5 and, ultimately, into the proximal end 8 of the cannula 6. The opening 9 in the capsule 5 is connected to the proximal end 8 of the cannula 6 by a flow channel, which is at least in part provided by a conduit 10 connected to the opening 9 and the proximal end 8 of the cannula 6. This is described in more detail below.

The cannula 6 may be controllably extendable and/or retractable through the exterior of the housing 2 in order to allow it to be safely stowed in the housing 2 when not in use. The device 1 may contain a user-operable actuator 11 to facilitate this. The actuator 11 is configured to cause movement of the cannula 6 relative to the housing 2 of the device 1 in order to extend and/or retract the cannula 6. An example is an actuator 11 that comprises a sprung element 12 and a switch 13 for releasing the sprung element 12. Upon release by the switch 13, the sprung element 12 may be configured to automatically extend and thereby drive the cannula 6 partially out of the housing 2 into an injection position. The actuator 11 may be electrically powered. For example, the switch 13 for releasing the sprung element 12 referred to above may be electrically powered. Electrical power may also be used to retract the sprung element 12 back to its original non-extended position, thereby also withdrawing the cannula 6. For this purpose, the actuator 11 may comprise an electrical motor 14 and a suitable drive mechanism coupled to the sprung element 12. The electrical power may be provided by a battery 15 or other power source in the device 1, which may be rechargeable.

In particular, the battery 15 may be rechargeable if the configuration of the device 1 is such that the capsule 5 of medicament is replaceable. In this type of configuration, the device 1 comprises a sterile part and a non-sterile part. The sterile part of the device 1 is replaceable and comprises the replaceable capsule 5. The non-sterile part of the device 1 is reusable and comprises reusable elements of the device 1. The elements in the non-sterile part may include, for example, a rechargeable battery 15. In general, the non-sterile part includes elements that do not need to be sterile for safe operation of the device 1 and can be safely reused. It will be appreciated, however, that there is no requirement for the elements that do not need to be sterile to be confined exclusively to the non-sterile part of the device 1. For example, it is possible for the battery 15 to be included with other replaceable elements in the sterile part of the device 1. In this configuration, the battery 15 is non-rechargeable since it is replaced each time the capsule 5 is replaced.

As will be explained in more detail below, the device 1 may comprise an electronic controller 16 which is configured to control operation of the actuator 11 and/or other elements of the device 1. The electronic controller 16 comprises a processor 28 and a memory 29 and may, for example, comprise an electronic microcontroller which is communicatively coupled to the actuator 11 and/or other elements of the device 1 using a system bus (not shown). The switch 13, motor 14, battery 15 and controller 16 are shown in the block diagram of the device 1 in FIG. 2, but are not shown in FIG. 1.

An alternative is for the actuator 11 to operate under the control of a timing element, such as a mechanical timer. The timing element may be a count-down timer. The elapse of a count-down period of the timing element may indicate that an event has occurred, such as the completion of an injection of a dose of medicament. The elapse of the count-down period may cause the actuator 11 to move the cannula 6 or other injection element, for example by withdrawing the cannula 6 back into the housing 2 of the device 1.

The distal end 7 of the cannula 6 may be sharpened to facilitate its insertion into the body tissue of the patient. Alternatively, the dispensing interface 4 may also comprise a separate needle (not shown) or trocar (not shown) for aiding the insertion of the distal end 7 of the cannula 6 into the body tissue. The needle may be controllably extendable and/or retractable from the housing 2 of the device 1 in a similar manner to the cannula 6 discussed above. The needle is configured to pierce the skin of the patient in order to allow the cannula 6 to move into the body tissue. The needle may, for example, be arranged to extend through the centre of the cannula 6. Once the skin has been pierced, the device 1 is configured to retract the needle back into the housing 2 before delivery of the medicament. In the case that the device 1 comprises a separate needle of the type described above, the device 1 may comprise an actuator similar to the one previously discussed in relation to the cannula 6 to facilitate the extension and retraction of the needle.

Another alternative is for the medicament to be delivered through the needle itself. In this case, the needle has properties which are similar to those of conventional injection needles. A proximal end of the needle is connected to the medicament reservoir 3 in a similar manner to the cannula 6 discussed above so that fluid medicament can flow through the needle into the body tissue of the patient. If the device 1 is configured in this manner, the cannula 6 may be omitted from the dispensing interface 4.

The flow of medicament into the cannula 6, or other injection element, is controlled by a flow control apparatus 17. As illustrated in FIG. 1, the flow control apparatus 17 may comprise a piston 18 which is moveable through the capsule 5 from one end to the other to drive medicament out of the capsule 5 through the opening 9 referred to above. A suitable drive mechanism (not shown) is mechanically coupled to the piston 18 and is operable to cause the piston 18 to move through the capsule 5. Movement of the piston 18 may be electrically powered. For example, an electric motor 19 may be connected to the drive mechanism. The electric motor 19 is powered by a power source in the device 1, such as the battery 15 referred to previously.

Additionally or alternatively, the flow control apparatus 17 may comprise a seal 20 at the opening 9 in the capsule 5 to prevent medicament from flowing out of the capsule 5 before it is intended that it should do so. The seal 20 is breakable, or openable in some other way, to allow medicament to move from the capsule 5 into the cannula 6 or other injection element via the conduit 10 referred to previously. The device 1 is configured to operate the flow control apparatus 17, for example by breaking the seal 20 and/or moving the piston 18, in response to a patient-initiated trigger, as explained below.

Figure 3:
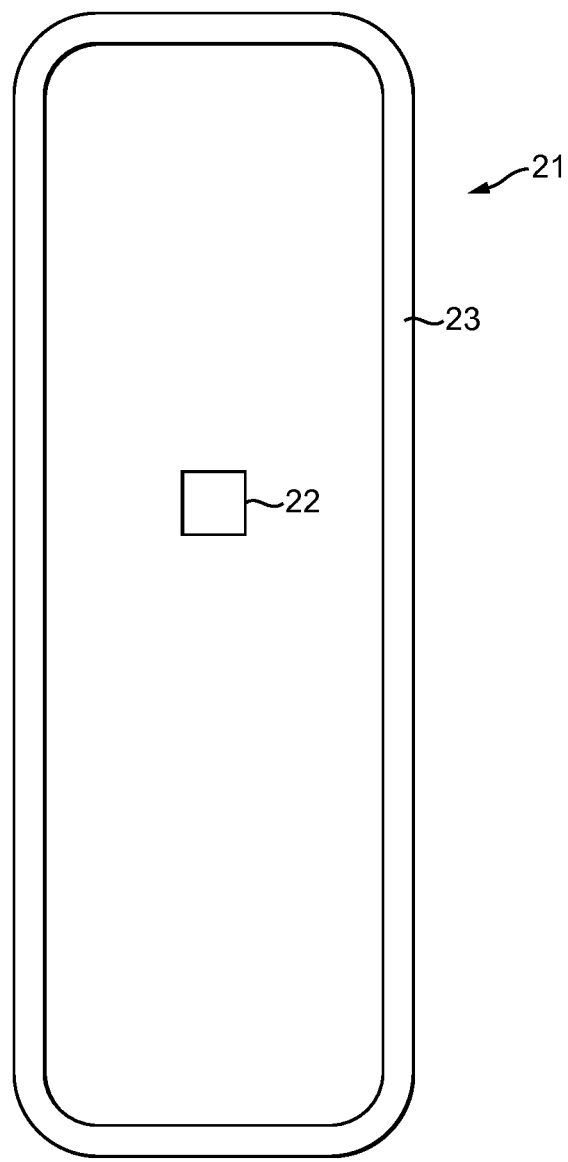
FIG. 3 is a schematic illustration of a patient contact region of a wearable device for delivering medicament to a user by injection.

Referring to FIG. 3, a contact region 21 of the housing 2 is arranged to be worn against the skin of the patient during use of the device 1. The contact region 21 may, for example, be located on a bottom face of the housing 2. The contact region 21 has geometric and tactile properties that are selected to be comfortable when worn against the skin of the patient. It is through the contact region 21 of the housing 2 that the cannula 6, or other injection element, protrudes into the body tissue of the patient during delivery of the medicament. The contact region 21 may, for example, comprise an aperture 22 through which the cannula 6 protrudes during use of the device 1. The aperture 22 is large enough to accommodate the cannula 6 and/or the separate needle referred to above, including during the extension and retraction operations previously described.

During use of the device 1, the contact region 21 is held against the skin of the patient by a fastener. The fastener is suitable for holding the contact region 21 in a stable position against the skin for a significant period of time, such as several hours, in order to ensure that the injection element is maintained in a fixed position relative to the body of the patient during use of the device 1. As shown in FIGS. 1 and 3, an example of a suitable fastener is an adhesive layer 23 for temporarily adhering the contact region 21 to the skin of the patient. The adhesive layer 23 may comprise a standard biocompatible glue, as used in common adhesive bandages. In order to protect the adhesive layer 23 from damage and to prevent it from sticking to unwanted objects prior to it being attached to the skin of the patient, the contact region 21 of the device 1 also includes a protective covering (not shown) which overlies the adhesive layer 23. The protective covering is selectively removable from the contact region 21 in order to expose the adhesive layer 23 before use of the device 1, for example by peeling the covering away from the adhesive layer 23.

Figure 4:
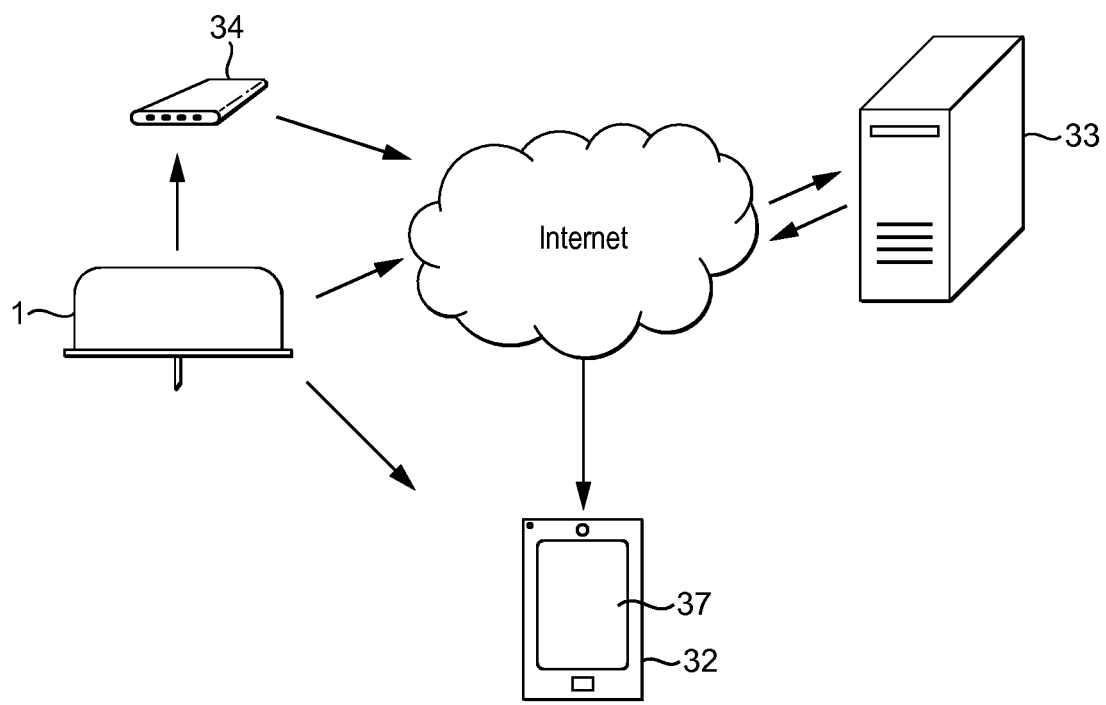
FIG. 4 is a schematic diagram showing communication connections between a wearable device for delivering medicament to a user by injection and a separate user device.

The device 1 also comprises a feedback apparatus 24 for providing feedback to the patient regarding the delivery of the medicament. The feedback apparatus 24 is configured to provide the feedback in a discreet manner so that the patient can be informed of the progress of the injection without the possibility of the feedback being noticed or shared by other people in the vicinity of the patient. The feedback apparatus 24 causes the feedback to be provided from the medicament delivery device 1 to a separate user device 32. The separate user device 32 is illustrated schematically in FIG. 4. Examples of the separate user device 32 include a cell phone, a smart phone, a smart watch, a tablet or other hand-held computer, a desktop computer, a laptop computer, or another type of personal computing device or interface. At the separate user device 32, the feedback may be displayed on a screen 37. The feedback apparatus 24 causes the feedback to be transmitted to the separate user device in response to detecting a request from the patient in the form of a physical interaction with the medicament delivery device 1. This involves the patient making physical contact with the medicament delivery device 1 in a predetermined manner. This predetermined manner is known to the medicament delivery device 1. As such, the medicament delivery device 1 is able to recognize the physical contact as corresponding to a request for feedback, as described in more detail below. The recognition of the physical contact as a request for feedback may be performed in the feedback apparatus 24, or may alternatively be performed elsewhere in the device 1.

The device 1 comprises a transducer 25 which is configured to detect physical inputs to the device 1 and to generate signals that are indicative of the detected physical inputs. The physical inputs may cause a degree of movement of the device 1 and the transducer 25 may be configured to detect the inputs by detecting these movements. The transducer 25 may comprise a motion sensor 26. An example of a suitable motion sensor 26 is an accelerometer, such as a piezoelectric accelerometer, although other types of motion sensors capable of sensing movement of the device 1 and generating a signal describing the detected movements could alternatively be used.

An example of a physical input that may be detected by the motion sensor 26 is a tap on the housing 2 of the device 1. This can be provided by the patient using a knuckle or finger tip. The tap on the housing 2 causes temporary movement in the device 1, for example in the form of a vibration. The movement caused by the tap is detected by the motion sensor 26, which is configured to generate a signal indicative of the detected movement. The type of movement in the device 1 caused by a tap on the housing 2 will generally have similar characteristics every time the housing 2 is tapped. This means that signals generated and output by the motion sensor 26 in response to taps on the housing 2 will all have similar characteristics. These similar characteristics allow the feedback apparatus 24 to distinguish a signal representing a tap on the housing 2 from signals representing other movements of the device 1.

The kinds of repeated signal characteristics described above are applicable not only to taps on the housing 2, but also to many other kinds of physical inputs to the device 1. An example of another kind of physical input is a prolonged finger-press by the patient against the housing 2 of the device 1. This may cause, for example, a prolonged deflection in the housing 2, which is detected by the motion sensor 26. The motion sensor 26 is configured to generate a signal which describes the deflection in the housing 2 in a similar manner to the signal described above in relation to a tap on the housing 2. The signal describing the deflection has characteristics that are significantly different from signals describing taps or other kinds of physical inputs to the device 1. This means that the feedback apparatus 24 can differentiate and identify the signal as being indicative of a prolonged finger-press on the housing 2.

The transducer 25 may additionally or alternatively comprise an electrical switch 27 on the exterior of the housing 2, which the patient can operate by providing a physical input to the switch 27. The physical input to the switch 27 connects electrical contacts in the switch. This causes the switch 27 to generate a signal which is communicated to the feedback apparatus 24. On the basis of the characteristics of the signal, the feedback apparatus 24 is configured to identify the signal as being indicative of an operation of the switch 27.

It will be appreciated from the discussion above that, in general, a signal generated by the transducer 25 in response to a physical input to the device 1 has characteristics that are associated with the particular kind of physical input received from the patient at the device 1.

The physical inputs involve deliberate and premeditated contact by the patient at the device 1. The signals are electrical signals and can be either analogue or digital. The signals are analysed by the feedback apparatus 24 to determine the physical input to which they correspond. In this way, the feedback apparatus 24 can differentiate between different requests for feedback from the user. The feedback apparatus 24 can also differentiate between contacts that are indicative of a request for feedback and contacts which are not, such as accidental contacts. This is explained in more detail below.

The device 1 comprises a communication coupling connected between the transducer 25 and the feedback apparatus 24. The signals generated by the transducer 25 are communicated to the feedback apparatus 24 via this communication coupling. Any suitable communication coupling can be used, such as an electrical connection on a printed circuit board or similar.

The feedback apparatus 24 may comprise the controller 16 referred to above. Upon receipt of a signal from the transducer 25, the controller 16 is configured to determine whether the signal is indicative of one or more pre-stored user inputs in the memory 29 of the controller 16. These pre-stored user inputs comprise user requests for information about the injection of the medicament. For example, the pre-stored user requests may generally be requests for information concerning the progress of the injection, such as a request for an indication of how long is remaining before the injection will be completed. Each pre-stored user request is linked, for example in a look-up table, in the memory 29 of the controller 16 to a pre-stored physical input. The physical inputs are stored in the memory 29 in the form of one or more signal characteristics associated with the physical input. These signal characteristics are those present in signals generated by the transducer 25 in response to receipt of the associated physical inputs at the device 1, as described above. Therefore, by matching the signal characteristics received from the transducer 25 with pre-stored characteristics in the memory 29, the controller 16 of the feedback apparatus 24 is able to recognize whether a pre-stored physical input has been detected at the device 1 and, if so, to identify the pre-stored user request that is associated with the detected physical input.

Upon recognizing a user input, the feedback apparatus 24 is configured to respond by causing appropriate feedback to be provided to the patient. Generating the feedback generally comprises the controller 16 identifying information in the memory 29 and using the information to compile an appropriate message for communication to the separate user device 32 referred to above. For example, in response to recognizing that the patient has requested an indication of the time of day at which the delivery of the medicament will be completed, the controller 16 may retrieve from the memory 29 the expected duration of the delivery process and the time of day at which the delivery process was commenced. The controller 16 may then calculate how long is remaining before the delivery of the medicament will be completed and compile a message containing this information.

Figure 2:
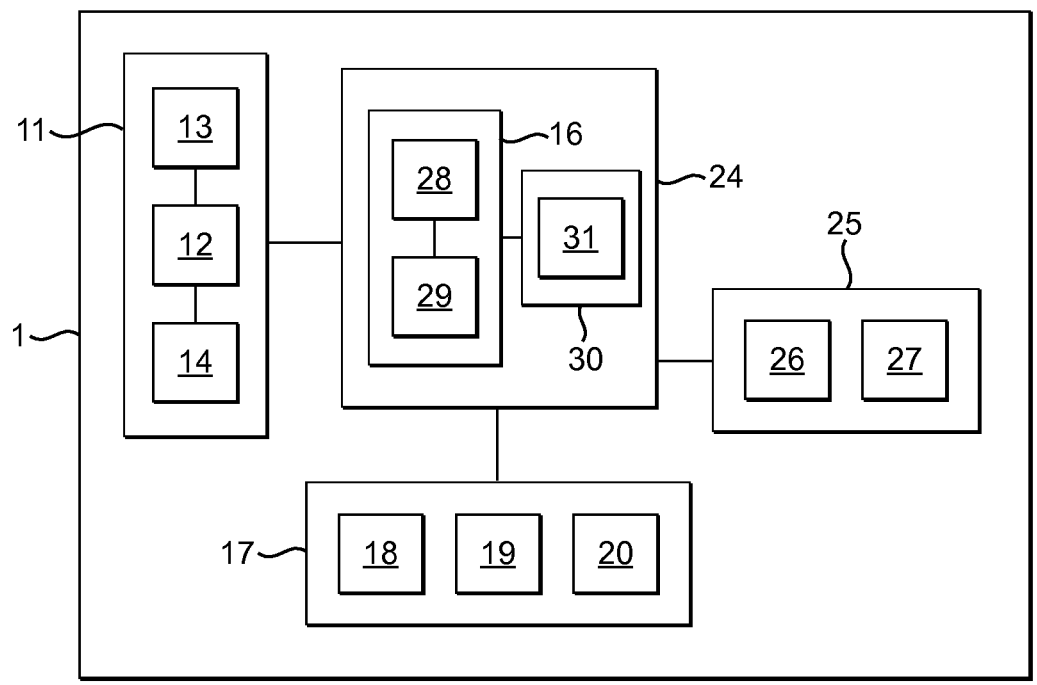
FIG. 2 is a block diagram of a wearable device for delivering medicament to a user by injection and providing discreet feedback to the user regarding the injection.

The device 1 also comprises a transmitter 30 for transmitting information to the separate user device 32 referred to above. Referring to FIG. 2, the transmitter 30 may for example comprise an antenna 31 for transmitting signals wirelessly to another device.

The medicament delivery device 1 comprises a communication coupling between the feedback apparatus 24 and the transmitter 30. Any suitable communication coupling can be used, such as an electrical connection on a printed circuit board or similar. The feedback apparatus 24 is configured to communicate with the transmitter 30 using this communication coupling to allow feedback to be transmitted to the user device 32. In particular, the transmitter 30 may be configured to receive a message from the feedback apparatus 24 and to transmit the message to the user device 32. The message may contain information assembled by the feedback apparatus 24 in response to recognition of a user request, as previously discussed.

The transmitter 30 may be configured to transmit the message to the separate user device 32 using a wireless communication coupling. The transmitter 30 may identify the user device 32 by performing a search for nearby user devices and transmitting the information to the closest user device identified in the search. For example, referring to FIG. 4, the transmitter 30 may be configured to transmit the message directly to the user device 32 using radio-based communication. The power of the radio signal may be low, so that it has an effective propagation distance that is small. This propagation distance is sufficient for the signal to be received in a high quality form at the separate user device 32, but may be insufficient for the signal to propagate much further. An example of a suitable distance is approximately one meter, since it is envisaged that the separate user device 32 will generally be on the patient's person or otherwise in very close proximity to the medicament delivery device 1.

The message is transmitted by the transmitter 30 using a suitable, known wireless communication protocol. An example of such a protocol is Bluetooth. An example of a standard that can be used for the communication is IEEE Standard 802.15.1-2002. Before transmitting the message, the transmitter 30 may be configured to initiate a pairing process with the separate user device 32 to establish a channel for sending the message.

Alternatively, the message may be transmitted to the user device 32 by SMS or over the Internet. Referring again to FIG. 4, the message may, for example, be transmitted from the transmitter 30 to a server 33 over the Internet. The communication between the transmitter 30 and the server 33 may be carried out in any suitable manner, such as over a 3G or 4G telecommunications network or through an ADSL via a Wi-Fi connection between the transmitter 30 and a wireless router and modem 34. The server 33 is configured to communicate the message to the user device 32 by any of these means, or similar.

The message may be encrypted by the transmitter 30 or feedback apparatus 24 before it is transmitted to the user device 32. This increases the security of the transmission.

In order to communicate the message to the separate user device 32, the server 33 may store an electronic address of the patient, or other user, in its memory. The address may comprise a cell phone number, an email address, a social media address, or similar. The address is accessible using the user device 32, for example by accessing an SMS, email or social media inbox. Messages received at the address can be caused to display on the screen 37 of the user device 32.

The electronic address may be registered with the server 33 beforehand. For example, upon first ownership of the medicament delivery device 1, the patient may register one or more electronic addresses in the server 33. The user may communicate the address(es) to the server 33 over the Internet or over another suitable communications link such as a 3G or 4G telecommunications network. The patient may at the same time communicate a serial number, or other unique identifier, of the medicament delivery device 1 to the server 33.

The server 33 may be configured to respond to this communication from the patient by linking the one or more electronic address(es) to the serial number, or other unique identifier, of the medicament delivery device 1 in the memory of the server 33. This allows the server 33 to communicate feedback received from the medicament delivery device 1 to the linked electronic address(es), as described below.

In one example, upon receiving a request for feedback in the manner previously described, the medicament delivery device 1 is configured to generate a message containing the feedback and a unique identifier of the medicament delivery device 1. The device 1 is configured to communicate the message to the server 33 using the transmitter 30 previously described. Upon receipt of the message, the server 33 is configured to read the unique identifier of the medicament delivery device 1 from the message and to look up the associated electronic address(es) stored in its memory. The server 33 is configured to then forward the message to the electronic address(es) for access by the patient using the user device 32. The user device 32 may be configured to periodically check the electronic address(es) and download recently received messages into a memory of the device 32. Alternatively, the messages may be pushed to the user device 32 automatically, for example by an email server.

This technique is secure in the sense that the unique identifier of the medicament delivery device 1 is communicated only to the server 33. The unique identifier is not communicated to the electronic address(es). Therefore, the unique identifier of the device 1 cannot be obtained by unauthorized access of the electronic address(es).

The server 33 may operate from a secure location and may be administered by, for example, the supplier of the medicament delivery device 1 to the patient.

The user device 32 may comprise a memory in which an application program is stored. The application program contains instructions that are executable by a processor of the user device 32. The application program is configured to access messages sent by the transmitter 30 of the medicament delivery device 1, for example by accessing the electronic address(es) referred to above, and to cause the information in the messages to be displayed on the screen 37 of the user device 32.

In this way, the patient is able to both request and receive the information in a discreet fashion.

Figure 5:
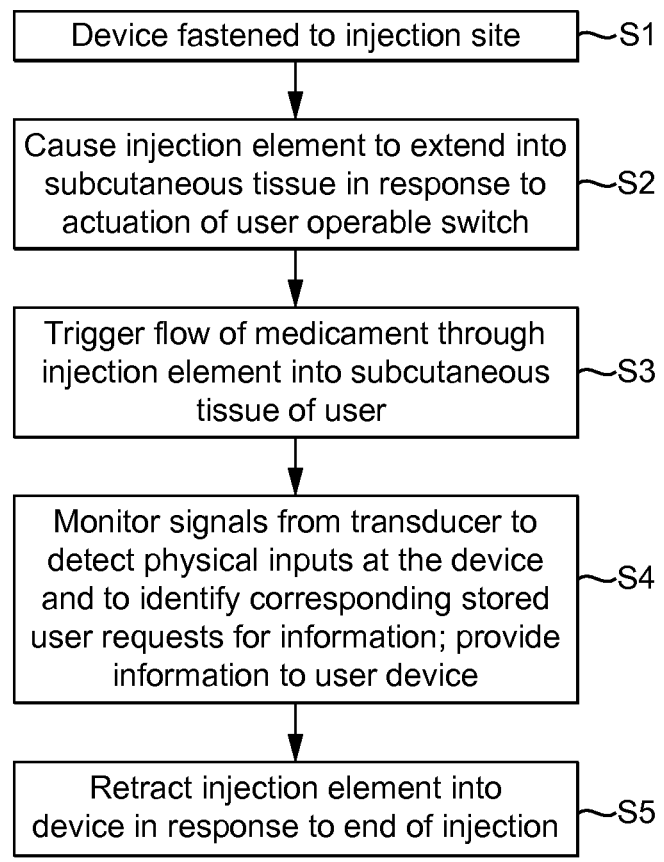
FIG. 5 is a flow diagram of a method of providing discreet feedback to a user regarding delivery of a medicament.

An example of a medicament injection and feedback process is described below with respect to FIG. 5. In a first step S1, the patient fastens the contact region 21 of the device 1 to an injection site on his or her body. The patient may, for example, peel the protective covering away from the adhesive layer 23 and press the adhesive layer 23 against his or her skin to adhere the device 1 to the injection site.

In a second step S2, the patient actuates a switch 38 on the housing 2 of the device 1 to begin delivery of the medicament. The device 1 is configured to respond by causing the cannula 6 or other injection element to extend through the aperture 22 in the housing 2 and into the body tissue of the patient. The device 1 may optionally comprise a sensor (not shown) that is configured to detect the position of the cannula 6 or other injection element and report the position to the controller 16. In this way, the controller 16 is informed of when the cannula 6 or other injection element has been fully extended through the aperture 22 in the housing 2 and is in position to inject the medicament into the body tissue.

In a third step S3, the flow control apparatus 17 is configured to begin dispensing a dose of medicament into the cannula 6 via the conduit 10. For example, the controller 16 may cause the power to be supplied from the battery 15 to the electric motor 19 coupled to the piston 18 in the capsule 5. The electric motor 19 drives movement of the piston 18 through the capsule 5 to expel a dose of medicament through the opening 9 in the far end of the capsule 5. If the flow control apparatus 17 comprises a seal 20 at the opening 9 of the capsule 5, this seal 20 is opened to allow the fluid medicament to be released into the first length of conduit 10. The seal 20 may be broken by fluid pressure in the capsule 5 caused by movement of the piston 18 or may be broken by some other means, such as an actuator (not shown) which moves in response to a signal from the controller 16 to pierce the seal 20.

The third step S3 may be triggered by a predetermined amount of time passing since operation of the switch 38 by the patient. Alternatively, the third step S3 may be triggered in response to the sensor referred to above detecting that the cannula 6 has been extended into the patient.

The device 1 may be configured to deliver the dose of medicament in a manner and at a rate which is dictated by the controller 16. For example, the dose may be administered to the patient in a continuous way at a pre-set rate. Alternatively, the dose may be administered to the patient in a plurality of discrete portions over a pre-set time period, or in any other manner, by appropriate movements of the piston 18.

In a fourth step S4, the feedback apparatus 24 is configured to monitor signals from the transducer 25 to detect physical inputs on the device 1 corresponding to requests for information from the patient. The feedback apparatus 24 identifies the requests by comparing signals from the transducer 25 with pre-stored signal characteristics indicative of physical inputs associated with the user requests, and identifying matches. In response to detecting a request for information, the feedback apparatus 24 compiles a message containing the information and causes it to be transmitted to a user device 32 of the patient via the transmitter 30. The information is displayed on the screen 37 of the user device 32 in the manner previously described.

In a fifth step S5, the controller 16 is configured to cause the actuator 11 to retract the cannula 6 out of the body tissue of the patient to end the medicament delivery process. Retraction of the cannula 6 or other injection element may cause the feedback apparatus 24 to disable itself. Retraction of the cannula 6 or other injection element may alternatively cause the feedback apparatus 24 to disable the transmitter 30. This ensures that the medicament delivery device 1 can not transmit feedback messages when the device 1 is not in use.

The disablements referred to above may additionally or alternatively be caused by detachment of the device 1 from the body of the patient. A suitable proximity sensor may be included in the contact region 21 in order to detect such detachment from the body. Alternatively, the disablements may be performed a predetermined amount of time after a trigger event, such as activation of the device 1 by actuation of the switch 38 on the housing 2.

It will be appreciated that the alternatives described can be used either singly or in combination.

Although the device 1 has been described in terms of comprising an automatically extending/retracting injection element, it will be appreciated that the injection element may be fixed so that it permanently protrudes through the housing. In these circumstances the injection element may be protected by a removable guard to minimise any danger of the element being damaged, or accidentally damaging something else, before use of the device. It will also be appreciated that in these circumstances the injection element is generally introduced into the patient's body tissue as the device is placed against the patient's skin, rather than as a subsequent step as described above. The injection element may comprise the cannula 6 described above or may comprise a needle. As indicated above, in one example the injection element comprises a trocar (which does not have a bore) of a cannula arrangement which leaves a flexible tube in the tissue of the patient but does not leave the needle in the user during the medicament delivery.

The operation of the device 1 has been described principally in terms of operating under the control of an electronic controller 16. However, where possible, individual elements of the device 1 may alternatively operate without the electronic controller 16. For example, the operation of certain elements may be triggered or otherwise controlled by a timing element such as a mechanical timer in the device 1. The timing element may be relatively simple and may comprise a count-down timer. The elapse of a fixed count-down period of the timing element may cause the elements to operate in a particular manner. For example, the timing element may cause the actuator 11 to extend and/or retract the cannula 6. Additionally or alternatively, a separate timing element may cause the flow control apparatus 17 to control a flow of medicament into the cannula 6, for example by commencing or ceasing the flow or by varying the flow rate.

The timing element may be configured to count down the fixed count-down period in response to the initial activation of the device 1 by the patient (e.g. following operation of the switch 38 referred to above). Alternatively, the timing element may be configured to count down the fixed count-down period in response to the extension of the cannula 6 or other injection element from the housing 2. Alternatively, the timing element may be configured to count down the fixed count-down period in response to the attachment of the contact region 21 of the device 1 to the body of the patient. One or more suitable proximity sensors in the contact region 21 may be used to determine when the device 1 has been attached.

The device 1 is described above as being configured to deliver the medicament subcutaneously. However, it may instead be configured for intradermal injection, for instance using a microneedle, or for injection in some other manner.

The bolus injector device may be of the type known as a Large Volume Device (LVD). An LVD injection device is configured to dispense a relatively large dose of medicament, in particular at least 1 ml and typically up to 2.5 ml, but possibly up to 10 ml.

The bolus injector device is configured to deliver a bolus of the respective medicament to bring a volume of the medicament into a patient's body within a predetermined time. The injection rate, however, may not be critical, i.e. tight control may not be necessary. However, there may be an upper (physiological) limit to the delivery rate in order to avoid damage to the tissue surrounding the delivery site. The time taken to deliver a bolus dose of medicament may be between a few minutes and many hours depending on a number of factors including the quantity (volume) of medicament, the viscosity of the medicament and the nature of the injection site at which the injection device is intended to be used.

From a user or Health Care Professional perspective, it is desirable for an injection device to be configured to minimally impact the patient's lifestyle and schedule, providing the patient with minimal reminder of his or her disease between the injections. The treatment schedule for therapies is usually intermittent, i.e. may be one injection per week, one injection every other week, or one per month. Therefore, the patient usually has no routine in dealing with his or her disease, and hence has minimal routine/experience in performing the required injections. Thus, configuration of the injection device to simplify its operation by patients is highly desirable.

Because it is intended for bolus operation, the configuration of the injection device is quite different compared to an injection device that is intended to be used for basal operation. Also, its use is quite different. For instance, a basal type insulin pump generally is relatively expensive as it includes many sophisticated diabetes specific features like programmable delivery rate profiles, bolus calculators etc. Further, the connection to the body via an infusion set allows the patient to handle and manipulate the pump in his/her field of view while the therapy is ongoing. Further, diabetes patients usually have a routine in setting-up the infusion set, connecting and operating the pump, and disconnecting the pump temporarily for events like taking a shower so not to expose the pump to water. In contrast, the bolus injector devices described above can be relatively simple and inexpensive devices. They may be provided as single-use devices, which cannot be recharged with medicament, which further reduces complexity and cost.

The actuators referred to above may comprise mechanical actuators, for example comprising one or more sprung elements. The actuators may alternatively comprise solenoids, piezo actuators, magnetic actuators or other mechanisms.

The term "drug" or "medicament", as used herein, means a pharmaceutical formulation containing at least one pharmaceutically active compound. In some embodiments, the pharmaceutically active compound can have a molecular weight up to 1500 Da or may include a peptide, a protein, a polysaccharide, a vaccine, a DNA molecule, an RNA molecule, an enzyme, an antibody or a fragment thereof, a hormone or an oligonucleotide, or a mixture of the above-mentioned pharmaceutically active compound. Various types or subtypes of compounds are also contemplated. For example, RNA may include RNAi, siRNA, or miRNA. In other embodiments, the pharmaceutically active compound can be useful for the treatment or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis or rheumatoid arthritis. In some embodiments, the pharmaceutically active compound can comprise at least one peptide for the treatment or prophylaxis of diabetes mellitus or complications associated with diabetes mellitus such as diabetic retinopathy. The pharmaceutically active compound can also comprise at least one human insulin or a human insulin analogue or derivative, glucagon-like peptide (GLP-1) or an analogue or derivative thereof, or exendin-3 or exendin-4 or an analogue or derivative of exendin-3 or exendin-4 or a pharmaceutically acceptable salt or solvate thereof.

Insulin analogues can include, for example, Gly(A21), Arg(B31), Arg(B32) human insulin; Lys(B3), Glu(B29) human insulin; Lys(B28), Pro(B29) human insulin; Asp (B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivatives can include, for example, B29-N-myristoyl-des(B30) human insulin; B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 can include, for example, Exendin-4(1-39).

Hormones can include, for example, hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, or Goserelin.

A polysaccharide can include, for example, a glucosaminoglycane, a hyaluronic acid, a heparin, a low molecular weight heparin or an ultra low molecular weight heparin or a derivative thereof, or a sulphated, e.g. a polysulphated form of the above-mentioned polysaccharides, and/or a pharmaceutically acceptable salt thereof. An example of a pharmaceutically acceptable salt of a polysulphated low molecular weight heparin is enoxaparin sodium.

Antibodies can include generally globular plasma proteins (~150 kDa) that are also known as immunoglobulins which share a basic structure. As they can have sugar chains added to amino acid residues, they may also be classified as glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that can include four polypeptide chains; two heavy chains and two light chains connected by disulfide bonds between cysteine residues. Each heavy chain can be about 440 amino acids long; each light chain can be about 220 amino acids long. Heavy and light chains may each contain intra-chain disulfide bonds which stabilize their folding. Each chain is composed of structural domains called Ig domains. These domains typically contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of antibodies can be similar, the unique property of a given antibody is determined by the variable (V) regions, as detailed above. More specifically, variable loops, often three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is usually the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their inter-chain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H inter-chain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion. Pharmaceutically acceptable solvates are for example hydrates.

In some embodiments, medicaments of various viscosities can be injected. For example, viscosity could range from about 3 to about 50 cP. In other embodiments, viscosity could be less than about 3 cP or greater than about 50 cP. Injection can further include delivering a medicament to a sub-cutaneous, an intra-muscular, or a transdermal location within a patient's body. The medicament can be in the form of a liquid, gel, slurry, suspension, particle, powder, or other type.

Typical injection volumes can range from about 1 mL to about 10 mL. Rates of injection may be about 0.5 mL/min, about 0.2 mL/min, or about 0.1 mL/min. Such injection profiles may be generally constant in flow rate, generally continuous in duration, or both generally constant and generally continuous. These injections can also occur in a single step of administration. Such injection profiles may be referred to as bolus injections.

Delivery devices functioning with such medicaments may utilize a needle, cannula, or other injection element configured to deliver a medicament to the patient, as previously discussed. Such an injection element may, for example, have an external size or diameter of 27 G or less. Further, the injection element could be rigid, flexible, and formed using a range of one or more materials. And in some embodiments, the injection element may include two or more components. For example, a rigid trocar may operate in conjunction with a flexible cannula as previously discussed. Initially, both the trocar and cannula may move together to pierce the skin. The trocar may then retract while the cannula remains at least partially within the target tissue. Later, the cannula may separately retract into the delivery device.

The insertion mechanism for inserting the insertion element may take any suitable form. As described above, it may be a mechanical spring based mechanism. Alternatively, the insertion element mechanism may for instance include an electric motor and a gear mechanism that causes insertion of the insertion element into the user. Alternatively, the insertion mechanism may be a gas or fluid pressure operated mechanism, in which case the needle driving energy source is either a reservoir of pressurised gas or a chemical system in which two or more chemicals are mixed together to produce gas or fluid pressure.

The invention claimed is:

1. A device configured to deliver a medicament to a user by injection, comprising:
   a housing with a contact region arranged to be worn against the skin of the user such that the housing is attached to the skin of the user;
   a transducer configured to detect a physical input to the housing during an injection and to generate a signal which is indicative of the detected physical input, wherein the transducer comprises a motion sensor configured to detect motion of the device caused by the physical input and to generate the signal as being indicative of the detected motion of the device;
   a feedback apparatus configured to respond to the signal by recognizing the physical input as being a user request for information regarding a progress of delivery of the medicament such that the user is able to request information regarding the progress of delivery of the medicament in a discreet manner by providing the physical input to the housing whilst the housing is attached to the skin of the user, wherein the feedback apparatus comprises a memory that stores data linking at least one stored physical input with at least one stored user request; and a transmitter configured to respond to the request by outputting information regarding the delivery of the medicament to a separate user device via a wireless communication link, wherein the transmitter comprises an antenna for transmitting information wirelessly to another device.

2. The device according to claim 1, wherein the device further comprises an injection element that protrudes out of the contact region of the housing.

3. The device according to claim 2, wherein the injection element is extendable and/or retractable from the housing.

4. The device according to claim 3, comprising an actuator configured to extend and/or retract the injection element from the housing, wherein the actuator comprises an electrical motor.

5. The device according to claim 3, configured such that, upon retraction of the injection element, the feedback apparatus and/or transmitter are disabled.

6. The device according to claim 1, wherein the device further comprises a fastener that is configured to hold the contact region against the skin of the user.

7. The device according to claim 6, wherein the fastener comprises an adhesive layer.

8. The device according to claim 1, wherein the device further comprises a reservoir for medicament that is disposed in the housing.

9. The device according to claim 8, wherein the reservoir of medicament is provided in a capsule secured inside an internal cavity of the housing.

10. The device according to claim 8, wherein the reservoir of medicament and the feedback apparatus are located within the housing.

11. The device according to claim 1, wherein the motion sensor comprises an accelerometer.

12. The device according to claim 1, wherein the transducer comprises an actuatable switch on a housing of the device.

13. The device according to claim 1, wherein the feedback apparatus is configured to recognize the physical input as being the user request by accessing the memory to identify a link between the detected physical input and a stored user request.

14. The device according to claim 1, wherein the physical input comprises at least one tap on a housing of the device.

15. The device according to claim 1, wherein the feedback apparatus is configured to recognize the user input as being a request for an indication of the remaining duration of the injection.

16. The device according to claim 1, wherein the transmitter is configured to output the information by searching for nearby user devices and transmitting the information to the closest user device identified in the search.

17. The device according to claim 1, wherein the transmitter is configured to precede outputting the information by initiating a wireless pairing process with the user device.

18. The device according to claim 1, wherein the transmitter is configured to transmit the information regarding the delivery of the medicament together with a unique identifier of the device.

19. The device according to claim 1, wherein the transmitter is configured to output the information in an encrypted form.

20. The device according to claim 1 and an application program for the separate user device which, when executed by a processor in the separate user device, causes the information output by the transmitter to be displayed.

21. A system comprising the device according to claim 1 and a reservoir of medicament to be delivered into the user by injection.

22. The device according to claim 1, wherein the device is a single-use device.

23. The device of claim 1, further comprising a proximity sensor configured to detect detachment of the contact region from the skin of the user, the device configured such that, upon detachment of the contact region from the skin of the user, the feedback apparatus and/or transmitter are disabled.

24. The device according to claim 1, wherein the transmitter is configured to respond to the request by outputting information regarding the delivery of the medicament to the separate user device via the wireless communication link such that the separate device displays the time of day at which the delivery of medicament will be completed.

25. A method of outputting information regarding the delivery of a medicament from a device configured to deliver the medicament to a user by injection and comprising a housing with a contact region arranged to be worn against the skin of the user, the method comprising:

positioning the housing such that the contact region is located against the skin of the user and the housing is attached to the skin of the user;

detecting a physical input to the housing during an injection using a transducer, wherein the transducer comprises a motion sensor configured to detect motion of the device caused by the physical input and to generate the signal as being indicative of the detected motion of the device;

generating a signal which is indicative of the detected physical input;

responding to the signal by recognizing the physical input as being a user request for information regarding a progress of delivery of the medicament such that the user is able to request information regarding the progress of delivery of the medicament in a discreet manner by providing the physical input to the housing whilst the housing is attached to the skin of the user; and responding to the request by outputting information regarding the progress of delivery of the medicament to a separate user device via a wireless communication link.

* * * * *